US00PP19673P3

(12) United States Plant Patent

Ferguson et al.

(10) Patent No.: US PP19,673 P3

(45) Date of Patent: Feb. 3, 2009

(54) STRAWBERRY PLANT NAMED 'DRISSTRAWTHREE'

(50) Latin Name: *Fragaria×ananassa*
Varietal Denomination: DrisStrawThree

(75) Inventors: Michael D. Ferguson, Moorpark, CA (US); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 47 days.

(21) Appl. No.: 11/821,016

(22) Filed: Jun. 21, 2007

(65) Prior Publication Data

US 2008/0320625 P1 Dec. 25, 2008

(51) Int. Cl.
*A01H 5/00* (2006.01)

(52) U.S. Cl. ..... Plt./209

(58) Field of Classification Search ..... Plt./209
See application file for complete search history.

(56) References Cited

U.S. PATENT DOCUMENTS

PP11,548 P * 10/2000 Amorao et al. ..... Plt./209
PP12,889 P2 * 8/2002 Lamb et al. ..... Plt./364
PP14,771 P3 * 5/2004 Amorao et al. ..... Plt./209
PP18,878 P2 * 6/2008 Mowrey et al. ..... Plt./209

OTHER PUBLICATIONS

UPOV Rom Gtitm Compuyter Database, GTI Jouve Reteieval Software, Feb. 2008 Citations for 'DrisStraw-Three'.*

* cited by examiner

*Primary Examiner*—Wendy C. Haas
(74) *Attorney, Agent, or Firm*—Jondle & Associates, P.C.

(57) ABSTRACT

This invention relates to a new and distinct cultivar of strawberry plant named 'DrisStrawThree'. The new cultivar is primarily characterized by its large fruit size, heavy fruit production, and resistance to powdery mildew.

3 Drawing Sheets

Genus and species: *Fragaria×ananassa*.
Variety denomination: 'DrisStrawThree'.

BACKGROUND OF THE NEW PLANT

The present invention relates to a new and distinct strawberry cultivar designated 'DrisStrawThree' and botanically known as *Fragaria×ananassa*. This new strawberry cultivar was discovered in October, 2002 and originated from a cross between the female parent '5F205', a proprietary strawberry plant (unpatented) and the male parent 'San Juan' (U.S. Plant Pat. No. 12,899). The original seedling of the new cultivar was asexually propagated at a nursery in Shasta County, Calif. 'DrisStrawThree' was subsequently asexually propagated and underwent further testing at a nursery in Ventura County, Calif. for four years. The present invention has been found to retain its distinctive characteristics through successive asexual propagations.

DESCRIPTION OF THE PHOTOGRAPHS

The accompanying color photographs show typical specimens of the new cultivar at various stages of development as nearly true as it is possible to make in color reproductions.

DESCRIPTION OF THE NEW CULTIVAR

Figure 1:
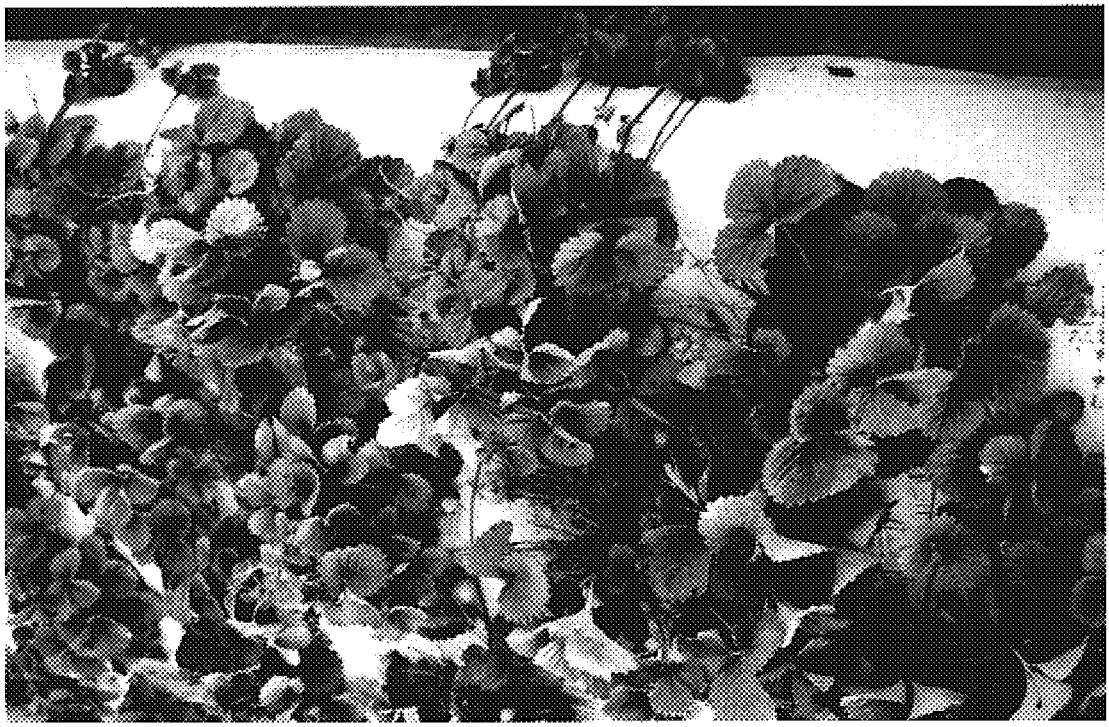
FIG. 1 shows overall plant habit including fruit at various stages of development.
Figure 2:
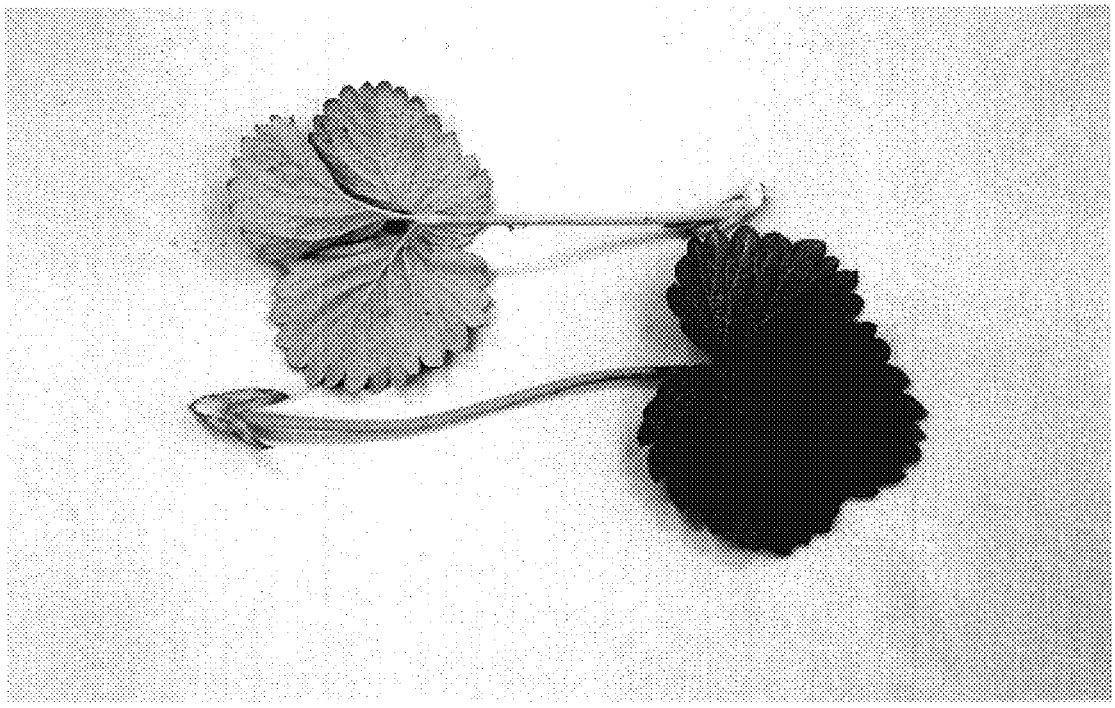
FIG. 2 shows leaves of the plant with three leaflets.
Figure 3:
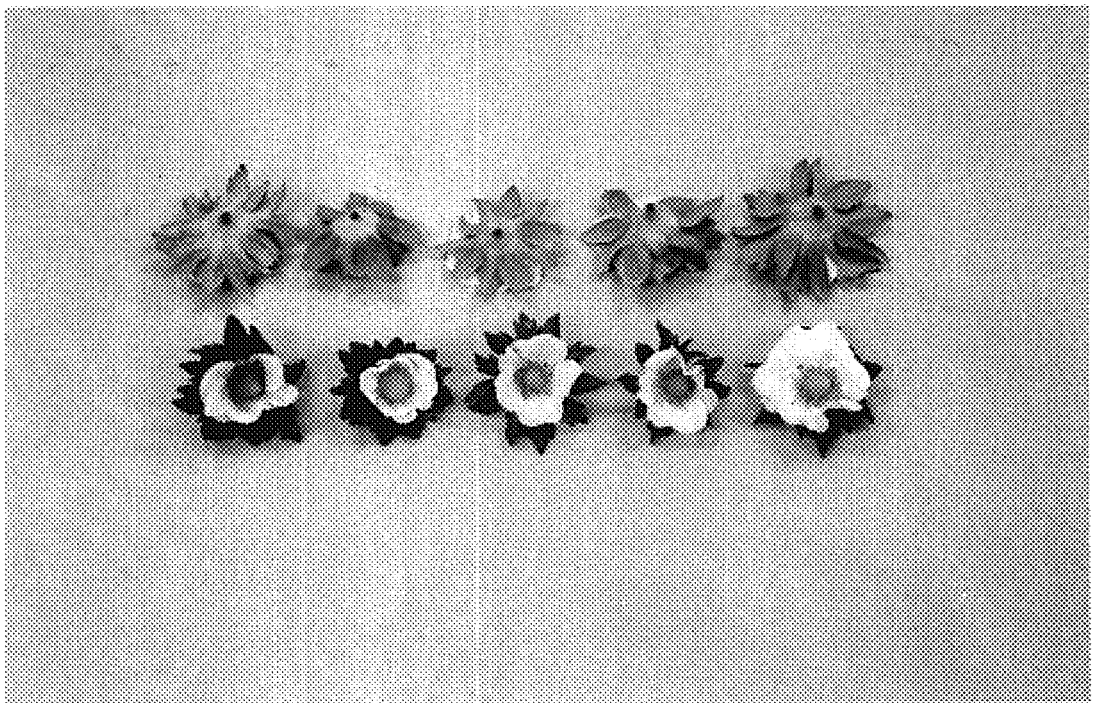
FIG. 3 shows both the upperside and underside of several of the flowers.
Figure 4:
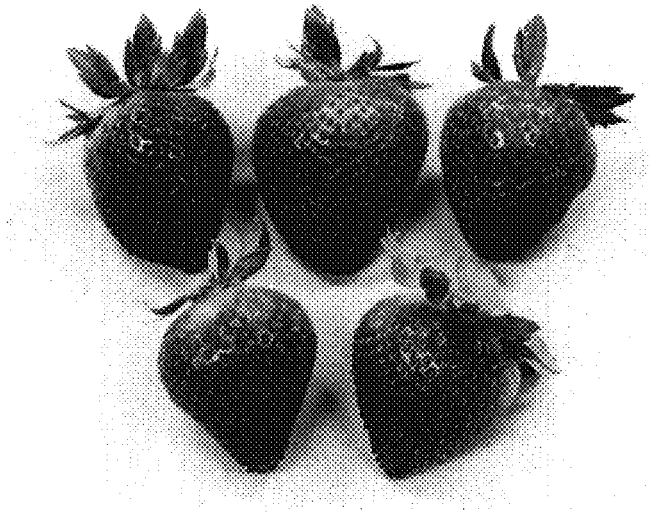
FIG. 4 shows the whole fruit.
Figure 5:
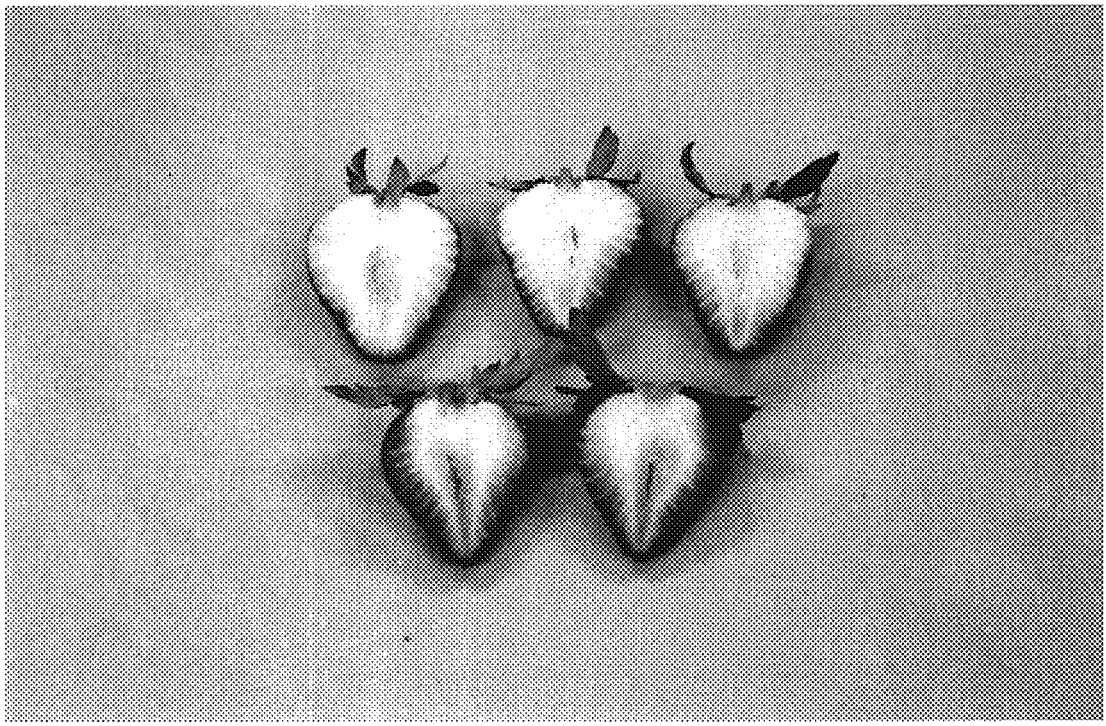
FIG. 5 shows the fruit in longitudinal cross-section.

The following description of 'DrisStrawThree' is based on observations taken from the 2002 to 2006 growing seasons in Ventura County, Calif. This description is in accordance with UPOV terminology. Color designations, color descriptions, and other phenotypical descriptions may deviate from the stated values and descriptions depending upon variation in environmental, seasonal, climatic and cultural conditions. 'DrisStrawThree' has not been observed under all possible environmental conditions. Color terminology follows the Royal Horticultural Society Colour Chart, London (R.H.S.) (2001).

DETAILED BOTANICAL DESCRIPTION

Table 1 shows plant characteristics of the new variety compared with plant characteristics of the parent 'San Juan'. Plant characteristics include plant height, leaf shape in cross section, fruit hollow center, fruit texture when tasted, and reaction to aphids.

TABLE 1

| Characteristic | 'DrisStrawThree' | 'San Juan' |
|---|---|---|
| Plant height (cm) | 20.5 | 28.0 |
| Leaf shape in cross | Slightly concave | Flat to slightly convex |
| Fruit hollow center | Small | Medium |
| Fruit texture when tasted | Very fine | Medium |
| *Aphis* spp. (Aphids) | Moderately resistant | Susceptible |

Table 2 shows plant characteristics of the new variety compared with plant characteristics of the commercial varieties, 'Driscoll Camarillo' (U.S. Plant Pat. No. 14,771) and 'Baeza' (U.S. Plant Pat. No. 11,548). Plant characteristics include plant height, diameter, number of crowns per plant, habit, density of individual plant and vigor.

TABLE 2

| Characteristic | 'DrisStrawThree' | 'Driscoll Camarillo' | 'Baeza' |
|---|---|---|---|
| Plant height (cm) | 20.5 | 23.3 | 22.4 |
| Plant diameter (cm) | 45.1 | 43.9 | 44.7 |
| Number of crowns/plant | 4 | 3 | 3 |
| Habit | Flat globose | Globose | Globose |
| Density of individual plant | Dense | Medium to Dense | Medium to Dense |
| Vigor | Strong | Strong | Medium |

Table 3 shows leaf characteristics of the new cultivar compared with leaf characteristics of 'Driscoll Camarillo' and 'Baeza'. Leaf characteristics include terminal leaflet length and width in centimeters, length to width ratio, number of teeth per terminal leaflet, shape of teeth, color of upperside and underside of leaf, leaf shape in cross section, leaf blistering, leaf glossiness, number of leaflets, leaflet margin, and shape of leaf base.

TABLE 3

| Leaf Characteristic | 'DrisStrawThree' | 'Driscoll Camarillo' | 'Baeza' |
|---|---|---|---|
| Terminal leaflet length (cm) | 0.82 | 0.90 | 0.83 |
| Terminal leaflet width (cm) | 0.80 | 0.97 | 0.91 |
| Terminal leaflet length/width ratio | 1.04 | 0.93 | 0.91 |
| No. teeth/ terminal leaflet | 17 | 27 | 29 |
| Shape of teeth | Rounded | Rounded | Rounded |
| Color of upperside of leaf | RHS 139A | RHS N189B | RHS 147A |
| Color of underside of leaf | RHS 191B | RHS 137C | RHS 137C |
| Leaf shape in cross section | Slightly concave | Slightly concave | Concave |
| Leaf blistering | Weak | Medium | Medium |
| Leaf glossiness | Weak | Weak | Weak |
| No. leaflets | Three only | Three only | Three only |
| Terminal leaflet margin | Revolute | Revolute | Revolute |
| Terminal leaflet base shape | Obtuse | Rounded | Rounded |

Table 4 shows information about the petiole, the petiolule, the bract, and the stipule of the new cultivar compared to 'Driscoll Camarillo' and 'Baeza'. This includes petiole length in centimeters, petiole diameter in centimeters, petiolule length in centimeters, petiolule diameter in centimeters, bract frequency per petiole, stipule length in centimeters, stipule width in centimeters, stipule pubescence, petiole pubescence, pose of hairs on the petiole, color of the petiole and color of the petiolule.

TABLE 4

| Characteristic | 'DrisStrawThree' | 'Driscoll Camarillo' | 'Baeza' |
|---|---|---|---|
| Petiole length (cm) | 14.1 | 12.7 | 13.4 |
| Petiole diameter (cm) | 0.412 | 0.408 | 0.420 |
| Petiole pubescence | Dense | Sparse | Medium to dense |
| Petiole pose of hairs | Outward to downward | Outwards | Outwards |
| Petiole color | RHS 144B | RHS 144B | RHS 144B |
| Petiolule color | RHS 145B | RHS 145B | RHS 145B |
| Petiolule length (cm) | 1.098 | 1.255 | 1.456 |
| Petiolule diameter (cm) | 0.236 | 0.254 | 0.232 |
| Bract frequency | 1 | 1 | 1 |
| Stipule length (cm) | 3.8 | 4.0 | 3.7 |
| Stipule width (cm) | 0.985 | 1.070 | 1.256 |
| Stipule pubescence | Dense | Sparse | Sparse |

Table 5 shows stolon characteristics of the new cultivar compared to 'Driscoll Camarillo' and 'Baeza'. These characteristics include the number of stolons, the anthocyanin coloration of the stolons, the thickness of the stolons, and the pubescence of the stolons.

TABLE 5

| Characteristic | 'DrisStrawThree' | 'Driscoll Camarillo' | 'Baeza' |
|---|---|---|---|
| Stolon Number | Few to medium | Few to medium | Few to medium |
| Stolon Anthocyanin | Strong | Weak to medium | Weak to medium |
| Stolon Thickness | Medium | Thick | Thick to very thick |
| Stolon Pubescence | Sparse | Sparse | Medium to dense |

Table 6 shows inflorescence characteristics of the new cultivar compared to 'Driscoll Camarillo' and 'Baeza'. These characteristics include inflorescence position relative to foliage, relative flower size, flower diameter in centimeters (measured from petal tip to petal tip), relative spacing of petals, petal length in centimeters, petal width in centimeters, petal length to width ratio, petal color, calyx diameter in centimeters (measured on back of flower from sepal tip to sepal tip), diameter of calyx relative to corolla, diameter of inner calyx relative to outer, sepal length in centimeters (measured from sepal tip to point of attachment to receptacle), sepal width in centimeters, receptacle color and anther color.

TABLE 6

| Characteristic | 'DrisStrawThree' | 'Driscoll Camarillo' | 'Baeza' |
|---|---|---|---|
| Inflorescence position relative to foliage | Beneath | Above | Above |
| Flower size | Medium | Medium | Medium |
| Flower diameter (cm) | 3.001 | 2.263 | 2.490 |
| Petal spacing | Overlapping | Overlapping | Overlapping |
| Petal length (cm) | 1.502 | 1.262 | 1.496 |

TABLE 6-continued

| Characteristic | 'DrisStrawThree' | 'Driscoll Camarillo' | 'Baeza' |
|---|---|---|---|
| Petal width (cm) | 1.531 | 1.263 | 1.511 |
| Petal length/width ratio | 0.98 | 1.00 | 0.99 |
| Petal color | RHS 155B | RHS 155C | RHS 155B |
| Calyx diameter (cm) | 4.088 | 2.550 | 2.925 |
| Calyx diameter relative to corolla | Larger | Smaller | Same size |
| Inner calyx diameter relative to outer | Same size | Same size | Same size |
| Sepal length (cm) | 1.582 | 0.964 | 1.087 |
| Sepal width (cm) | 0.817 | 0.544 | 0.505 |
| Receptacle color | RHS N144A | RHS 2B | RHS 1A |
| Anther color | RHS 17A | RHS 15B | RHS 17B |

Table 7 shows fruit characteristics of the new cultivar compared to 'Driscoll Camarillo' and 'Baeza'.

TABLE 7

| Characteristic | 'DrisStrawThree' | 'Driscoll Camarillo' | 'Baeza' |
|---|---|---|---|
| Fruiting truss length (cm) | 13.4 | 26.5 | 21.7 |
| Fruiting truss attitude | Prostrate | Erect | Erect |
| Fruiting truss length | Medium | Long | Long |
| Fruit length (cm) | 4.93 | 3.76 | 4.35 |
| Fruit width (cm) | 4.36 | 3.73 | 3.92 |
| Fruit length/ width ratio | 1.13 | 1.01 | 1.11 |
| Fruit weight (g) | 27.5 | 21.0 | 22.3 |
| Relative fruit size | Very large | Medium | Medium |
| Predominant fruit shape | Almost cylindrical | Conical | Conical |
| Difference in shape between primary & secondary fruits | Slight | None or very slight | None or very slight |
| Band without achenes | Narrow | Absent or very narrow | Absent or very narrow |
| Unevenness of fruit surface | Medium | Medium | Medium |
| Fruit skin color | RHS 45B Red | RHS 46A Red | RHS 46B Red |
| Evenness of fruit color | Uneven | Even | Even |
| Fruit glossiness | Medium | Medium | Medium |
| Insertion of achenes | Level with surface | Level with surface | Level with surface |
| Achene coloration-sunward side of berry | RHS 165A Red to purple, possibly greyed | RHS 166B Red to purple, possibly greyed | RHS 163B Red to purple, possibly greyed |
| Achene coloration-shaded side of berry | RHS 151C yellow to green | RHS 151C yellow to green | RHS 151A Yellow to green |
| Achenes per berry | 243.6 | 316.2 | 361.3 |
| Achene weight | 0.000664409 | 0.000570367 | 0.000466731 |
| Insertion of calyx | Set above the fruit | Level | Level |
| Pose of calyx segments | Reflexed | Reflexed | Reflexed |

TABLE 7-continued

| Characteristic | 'DrisStrawThree' | 'Driscoll Camarillo' | 'Baeza' |
|---|---|---|---|
| Size of calyx in relation to fruit | Smaller to larger | Same size | Same size |
| Adherence of calyx | Strong | Strong | Strong |
| Firmness of flesh | Firm | Firm | Firm |
| Color of the flesh | RHS 155A (White) to RHS 44D (light red) | RHS 155A (White) to RHS 44D (light red) | RHS 155A (White) to RHS 38B (pale rose) |
| Evenness of flesh color | Slightly uneven | Even | Even |
| Distribution of flesh color | Marginal and central | Only marginal | Only marginal |
| Hollow center | Small | Absent | Medium |
| Sweetness | Strong | Medium | Medium |
| Acidity | Weak | Medium | Medium |
| Texture when tasted | Very fine | Medium | Medium |
| Time of flowering | Early | Early | Late |
| Harvest maturity | Mid-season, early June to late December | Mid-season, early June to late December | Late early July to late December |
| Type of bearing | Fully everbearing | Fully everbearing | Fully everbearing |
| Grams of fruit/plant | 500 | 286 | 289 |

Table 8 shows the resistance to different forms of stress of the new cultivar compared to 'Driscoll Camarillo' and 'Baeza'. These forms of stress include drought, high temperatures, wind, high pH, and high soil salt level.

TABLE 8

| Reaction to Stress | 'DrisStrawThree' | 'Driscoll Camarillo' | 'Baeza' |
|---|---|---|---|
| Drought | Moderately resistant | Moderately resistant | Moderately resistant |
| High temperatures | Moderately resistant | Moderately resistant | Moderately resistant |
| Wind | Moderately resistant | Moderately resistant | Moderately resistant |
| High pH | Moderately resistant | Moderately resistant | Moderately resistant |
| High soil salt level | Moderately resistant | Moderately resistant | Susceptible |

Table 9 shows pest and disease characteristics of the new cultivar compared to 'Driscoll Camarillo' and 'Baeza'.

TABLE 9

| Pest or Disease | 'DrisStrawThree' | 'Driscoll Camarillo' | 'Baeza' |
|---|---|---|---|
| *Tetranychus urticae* (2-spotted spider mite) | Moderately resistant | Moderately resistant | Moderately resistant |
| *Tarsonemus pallidus* | Moderately resistant | Moderately resistant | Moderately resistant |
| *Aphelencoides fragariae* | Moderately resistant | Moderately resistant | Moderately resistant |
| *Pratylenchus penetrans* | Moderately resistant | Moderately resistant | Moderately resistant |
| *Ditylenchus dipsac* | Moderately resistant | Moderately resistant | Moderately resistant |

TABLE 9-continued

| Pest or Disease | 'DrisStrawThree' | 'Driscoll Camarillo' | 'Baeza' |
|---|---|---|---|
| *Anthonomus rubi* | Moderately resistant | Moderately resistant | Moderately resistant |
| *Aphis* spp. (Aphids) | Moderately resistant | Moderately resistant | Moderately resistant |
| *Lygus hesperus* (Lygus bug) | Moderately resistant | Moderately resistant | Moderately resistant |
| Botrytis fruit rot | Moderately Susceptible | Moderately Susceptible | Moderately Susceptible |
| Powdery mildew | Resistant | Highly susceptible | Susceptible |

We claim:

1. A new and distinct cultivar of strawberry plant as described and shown herein.

* * * * *